(12) United States Patent
Tseng

(10) Patent No.: US 6,395,580 B1
(45) Date of Patent: May 28, 2002

(54) BACKSIDE FAILURE ANALYSIS FOR BGA PACKAGE

(75) Inventor: Fouriers Tseng, Tsin-Chu (TW)

(73) Assignee: Taiwan Semiconductor Manufacturing Company, Ltd., Hsin Chu (TW)

(*) Notice: Subject to any disclaimer, the term of this patent is extended or adjusted under 35 U.S.C. 154(b) by 0 days.

(21) Appl. No.: 09/450,143

(22) Filed: Nov. 29, 1999

(51) Int. Cl.$^7$ ............... H01L 21/44; H01L 21/48; H01L 21/50

(52) U.S. Cl. ............... 438/108; 438/14; 438/121; 438/613

(58) Field of Search ............... 438/106, 108, 438/112, 121, 122, 613, 14

(56) References Cited

U.S. PATENT DOCUMENTS 5,985,695 A * 11/1999 Freyman et al.
6,168,960 B1 * 1/2001 Li \* cited by examiner Primary Examiner—Kevin M. Picardat
Assistant Examiner—D. M. Collins
(74) Attorney, Agent, or Firm—Tung & Associates

(57) ABSTRACT

A method for conducting a backside failure analysis on a ball grid array (BGA) package that does not require a chemical etching step is described. In the method, a substrate can first be removed mechanically from the BGA package to expose a plastic encapsulated IC chip. The molding compound on the backside of the IC chip can then be removed by a mechanical method such as polishing or preferably, chemical mechanical polishing. Simultaneously with the exposure of the backside of the IC chip, the ends of a plurality of bonding wires which are connected to the bond pads on the top surface of the IC chip is also exposed. A plurality of probe needles or a bonder can then be used to make electrical contact with the ends of the bonding wires such that signals may be fed into the IC chip for conducting a failure analysis. The present invention novel method provides the advantage that the observation for the failure sites and the electrical connections to the IC chip can all be conducted on the same surface of the package and thus be carried out at low cost and in a simplified manner.

20 Claims, 2 Drawing Sheets

BACKSIDE FAILURE ANALYSIS FOR BGA PACKAGE

FIELD OF THE INVENTION

The present invention generally relates to a method for conducting a backside failure analysis on a ball grid array (BGA) package that requires a bias voltage input and more particularly, relates to a method for conducting a backside failure analysis on a BGA package that requires a bias voltage input by mechanically removing an IC chip encapsulated in a plastic compound from a substrate, and then polishing by a mechanical method the backside of the IC chip to remove the molding compound and to expose a naked surface of the IC backside and a plurality of bonding wires for connection to probe tips or to wire bonds from a bonder.

BACKGROUND OF THE INVENTION

In the semiconductor fabrication technology, the capability and effectiveness of performing a failure analysis on a semiconductor chip package are very important. When an integrated circuit (IC) chip fails in service, the nature and the cause for such failure must be determined in order to prevent the reoccurrence of such failure in similar products.

An IC chip is normally built on a silicon base substrate with many layers of insulating materials and metal interconnections. This type of multi-layer structure becomes more important in modem IC devices such as high density memory chips where, in order to save chip real estate, the active device is built upwards in many layers forming transistors, capacitors and other logic components.

When an IC device is found defective during a quality control test, various failure analysis techniques can be used to determine the cause of such failure. Two of the more recently developed techniques for performing failure analysis are the infrared light emission microscopy and the light-induced voltage alteration (LIVA) imaging technique. In the infrared light emission light analysis, an infrared light transmitted through a substrate silicon material is used to observe from the backside of an IC the failure mode of the circuit. For instance, at a magnification ratio of 100x, a failure site in the circuitry can be located. The LIVA imaging technique can be used to locate open-circuited and damaged junctions and to image transistor logic states. The LIVA images are produced by monitoring the voltage fluctuation of a constant current power supply when a laser beam is scanned over an IC. A high selectivity for locating defects is possible with the LIVA technique.

Another method that has become more common in failure analysis of IC chips is the scanning optical microscopy (SOM). The high focusing capability of SOM provides improved image resolution and depth comparable to conventional optical microscopy. It is a useful tool based on the laser beam's interaction with the IC. The SOM technique enables the localization of photocurrents to produce optical beam induced current image that show junction regions and transistor logic states. Several major benefits are made possible by the SOM method when compared to a conventional scanning electron microscopy analysis. For instance, the benefits include the relative ease of making IC electrical connection, the no longer required vacuum system and the absence of ionizing radiation effects.

Even though the above discussed techniques are effective in identifying failure modes in IC circuits, the techniques require elaborate and complicated electronic equipment which are generally costly and not readily available in a semiconductor fabrication facility. It is therefore desirable to have available a method and apparatus that can be easily carried out without expensive laboratory equipment such that the apparatus can be installed in any fabrication facilities. One such apparatus utilizes a liquid crystal coating layer for the identification of failure sites in an IC chip. For instance, in the method wherein a liquid crystal layer is used for the identification of failure sites, a liquid crystal material is frequently coated on top of an IC chip or an IC package. A typical test set up is shown in FIG. 1.

As shown in FIG. 1, a typical liquid crystal detection apparatus 10 is provided. The apparatus 10 generally includes a heater 12 and an optical microscope 14. On a top surface 16 of the heater 12, an IC package 20 is positioned under the microscope 14. The IC package 20 may be a plastic quad flat pack (PQFP) or any other packaged IC device. The IC package 20, shown in FIG. 1, is completed with bonding pads 22 and bonding wires 24. In the middle portion of the package 20 are IC circuits that contain failure sites needed to be identified by a liquid crystal method. In the conventional method, a liquid crystal material is first coated on the top surface 26 of the IC package 20. The IC package 20 is then positioned on top of the heater 12 which can be heated at a pre-programmed heating rate to a specific temperature. The IC package 20, together with the coated liquid crystal layer (not shown) is normally heated to a temperature just below the clear/opaque transition temperature of the liquid crystal material. For instance, a suitable temperature would be approximately between about 5° and about 10° below the transition temperature of the liquid crystal. After the IC package 20 is heated to the predetermined temperature, a pre-selected voltage is applied to the IC circuit through bonding wires 24. The IC circuit, upon receiving such a voltage, heats up at any short or leakage positions. A hot spot is thus generated at each of the locations. The liquid crystal material immediately adjacent, or contacting the hot spots has its temperature raised above its transition temperature and transforms from an opaque state to a clear state. As a result, bright spots in the liquid crystal layer, i.e., on the IC package, show up to indicate the failure sites in the package.

Several drawbacks have been noted in the practice of the liquid crystal detection method. One of the obvious drawbacks is that when testing IC chips of different sizes, a single test board cannot be used for all IC chips. A different test board is required for testing chips of different sizes such that the chip can be mounted on the board for making electrical connections by wire bonding with the conductive leads provided on the test board. Based on the large number of IC chips of different sizes it is a tedious task to supply a large number of test boards that will fit each individual chip. Ideally, a universal test board should be designed such that it will fit different sizes of IC chips for testing.

Regardless which one of the failure analysis techniques is adopted, an IC chip package must be properly prepared with a suitable surface for performing a failure analysis. Since most modern IC chips utilizes at least two or more layers of metal thin films as interconnect layers, the active components of the chip on which the failure analysis is to be performed are usually shielded by the metal interconnect layers. Great difficulties are encountered in performing any of the failure analysis techniques, i.e., the infrared light emission microscopy, the LIVA imaging technique or the SOM technique, which cannot penetrate the layers of metals to detect the failure mode in the circuit.

In another more recently developed package for IC chips, i.e., the lead-on-chip (LOC) package, both the lead frame and the bonding wires are positioned on top of an IC circuit. The LOC package has been used in modern high density memory devices wherein a plurality of finger leads are disposed on and attached to an active surface of an IC chip. The benefits of using a LOC package is that the ratio between the size of an IC chip and the size of a package (which encapsulates the chip) is significantly higher than conventional packages since the mounting area (die pad) is no longer required in a LOC package. A high ratio between the chip size and the package size is very desirable in the ever increasing miniaturization of IC devices. A metal lead frame is normally used in a LOC package which substantially covers the active device.

Attempts have been made by others to perform failure analysis on the back surface of an IC chip package. For instance, the back surface of an IC chip package can be polished away to remove the encapsulating material and to expose the die back. A typical backside failure analysis conducted on an IC chip in an emission microscope is shown in FIG. 2. An emission microscope is an instrument that provides the location of localized light emissions in a field. The instrument is normally used for observing visible light emitted from voltage biased faulty semiconductor devices without the need for studying semiconductor materials directly. In order to examine the spectra distribution of the localized emissions and to determine the type of defects most likely caused the emission, a series of narrow band optical filters may be utilized in the light path of the microscope. The emission microscope is useful in studying the backside of an IC chip that is formed with multiple layers of conducting metals, such as in a transistor that is arranged under the multiple layers. In such a structure, it is difficult to detect emission from the front surface of the device and thus, necessitates the technique of backside failure analysis as shown in FIG. 2. By using an infrared light transmitted through the silicon layer of the IC device (which is transparent to IR), an observation from the backside of the IC is possible for failure site identification.

A problem that frequently occurs in the test method shown in FIG. 2 is that the lead frame connecting the IC circuit can be easily damaged during the polishing process. A damaged lead frame cannot be electrically connected by soldering to a printed circuit board or by clamping to a test socket. As a consequence, a bias voltage which is required for performing the failure analysis cannot be applied to the circuit. The problem of making an electrical connection to the circuit to be tested therefore renders the performance of a failure analysis impossible.

In still another test for failure analysis utilized for BGA packages, a strong acid is used to boil away (or dissolve) a plastic encapsulating compound and a substrate that the BGA package is attached to in order to obtain a naked IC chip. In this chemical etching method, a strong acid of hydrogen sulfide (a mixture of $H_2SO_4$ and $SO_3$) is used to completely etch away a plastic molding compound which is used to encapsulate the IC chip and a plastic substrate onto which the plastic molding compound is bonded to. A BGA package can thus be de-capped to produce an IC chip that has gold wires and gold bumps stilled connected. After the chemical etching process, the gold wires and the gold bumps are mechanically removed such that new wire bonds can be made to the bond pads for connecting to a probe tester to conduct the failure analysis. The chemical etching process for preparing a backside analysis on a BGA package is labor intensive and time consuming. Additionally, the IC chip which has the gold wires bonded on top of the gold bumps can be easily damaged during such sample preparation process.

It is therefore an object of the present invention to provide a method for conducting a backside failure analysis that requires a bias voltage input without the drawbacks or shortcomings of the conventional failure analysis methods.

It is another object of the present invention to provide a method for conducting a backside failure analysis on a BGA package that can be carried out without the need for removing all encapsulating compound.

It is a further object of the present invention to provide a method for conducting a backside failure analysis on a BGA package without the need for a strong acid in a chemical etching step.

It is another further object of the present invention to provide a method for conducting a backside failure analysis on a BGA package by first tearing off a substrate from a plastic encapsulated IC chip that is mounted on the substrate.

It is still another object of the present invention to provide a method for conducting a backside failure analysis on a BGA package by exposing a backside of an IC chip by a mechanical polishing method.

It is yet another object of the present invention to provide a method for conducting a backside failure analysis on a BGA package by removing encapsulating compound from the backside of an IC chip by a chemical mechanical polishing method.

It is still another further object of the present invention to provide a method for conducting a backside failure analysis on a BGA package by exposing a backside of an IC chip and a plurality of bonding wires by a chemical mechanical polishing method.

It is yet another further object of the present invention to provide a method for conducting a backside failure analysis on a BGA package by first removing encapsulating compound from the backside of an IC chip to expose the backside surface and a plurality of bond wires and then contacting the bond wires with probe tips for sending signals into the IC chip.

SUMMARY OF THE INVENTION

A method for conducting a backside failure analysis on a ball grid array (BGA) package which does not require a chemical etching step, but instead requires a chemical mechanical polishing method to expose bond wires for probing with probe tips is disclosed.

In a preferred embodiment, a method for conducting a backside failure analysis on a BGA package can be carried out by the operating steps of providing a BGA package which includes an IC chip encapsulated in a molding compound and joined to a top surface of a substrate by the molding compound. The IC chip has a backside facing the substrate and an active side, separating the substrate from the IC chip by severing a joint between the top surface of the substrate and the molding compound, removing the molding compound from the backside of the IC chip such that the backside of the IC chip and a plurality of bonding wires surrounding the chip are exposed, contacting the plurality of bonding wires with a plurality of probes such that electrical signals are fed into the IC chip, and observing failure sites on the exposed backside of the IC chip.

The method for conducting a backside failure analysis on a BGA package may further include the step of electrically connecting a plurality of bond pads on the IC chip to a plurality of conductive pads on the top surface of the substrate by a wire bonding technique. The method may further include the step of electrically connecting a plurality of bond pads on the IC chip to a plurality of conductive pads on the top surface of the substrate by wires that are made of gold or of gold alloy. The method may further include the step of mechanically separating the substrate from the IC chip, or the step of tearing the substrate from the IC chip.

The method for conducting a backside failure analysis on a ball grid array package may further include the step of removing the molding compound from the backside of the IC chip by a mechanical method, or by a polishing method, or by a chemical mechanical polishing method. The method may further include the step of contacting the plurality of bond wires with a plurality of probe tips. The method may further include the step of contacting the plurality of bond wires with wire bonds from a bonder. The method may further include the step of feeding a bias voltage into the IC chip through the plurality of probes. The method may further include the step of observing the failure sites on the exposed backside of the IC chip by a microscope.

In another preferred embodiment, the present invention provides a method for observing failure sites on the backside of a ball grid array (BGA) package which can be carried out by the steps of providing a BGA package of an IC chip encapsulated in a molding compound, the IC chip is joined to a substrate by a layer of the molding compound and by a plurality of bonding wires, severing a joint formed between the layer of molding compound and a top surface of the substrate, mechanically removing the layer of molding compound from the backside of the IC chip to expose the backside of the IC chip and the plurality of bonding wires, feeding a bias voltage into the IC chip through the plurality of bonding wires, and observing failure sites on the backside of the IC chip.

The method for observing failure sites on the backside of a BGA package may further include the step of joining the IC chip to the substrate by a plurality of bonding wires that includes gold. The method may further include the step of encapsulating the IC chip in a molding compound that includes plastic. The method may further include the step of severing the joint between the layer of molding compound and the backside of the IC chip by tearing the IC chip from the substrate. The method may further include the step of removing the layer of molding compound from the backside of the IC chip by a chemical mechanical polishing method. The method may further include the step of feeding the bias voltage into the IC chip through a plurality of probe tips, or by contacting the plurality of bonding wires with wires from a bonder. The method may further include the step of observing the failure sites on the backside of the IC chip by an optical method.

BRIEF DESCRIPTION OF THE DRAWINGS

These objects, features and advantages will become apparent by an examination of the following specification and the appended drawings in which.

DETAILED DESCRIPTION OF THE PREFERRED EMBODIMENT

The present invention discloses a method for conducting a backside failure analysis on a ball grid array package that requires a bias voltage to be fed as a VCC or a clock signal into a defective IC chip. The present invention novel method can be executed on the backside of an IC chip with simplicity and at low cost without damaging the chip itself. The method can be advantageously carried out by first removing mechanically a substrate from the BGA package, such as by tearing it off. The residual molding compound left on the backside of the IC chip is then polished away by a mechanical method. A suitable mechanical method for such material removal is a chemical mechanical polishing method which can be advantageously carried out at low cost and in a short time period. The bonding wires exposed in the encapsulating molding compound which surrounds the IC chip can then be connected to probe tips, or to bonding wires from a bonder for feeding signals such as a bias voltage into the chip for testing. The failure sites on the backside of the chip can be observed either with naked eyes or with an optical microscope. A suitable optical microscope to be used in the present invention novel method may be an IR CCD, an emission microscope or a visible light CCD. The present invention novel test method may further be utilized in an optical beam induced current technique by using an IR laser, or in an optical beam induced resistance change technique by using an IR laser. While the novel method can be used for any type of failure analysis, it is particularly suitable for use in techniques that only require simple bias conditions, for instance, those that require a simple bias voltage to be fed into a defective IC die. The simple bias voltage may be one suitable for VCC or for clock signal. The present invention novel method can be simply executed for sample preparation in a failure analysis conducted on the backside of an IC chip.

Numerous advantages are provided by the present invention novel method which include shortened sample preparation time, shortened sample analysis time and the capability of conducting a failure analysis without a wet etching process.

Figure 1:
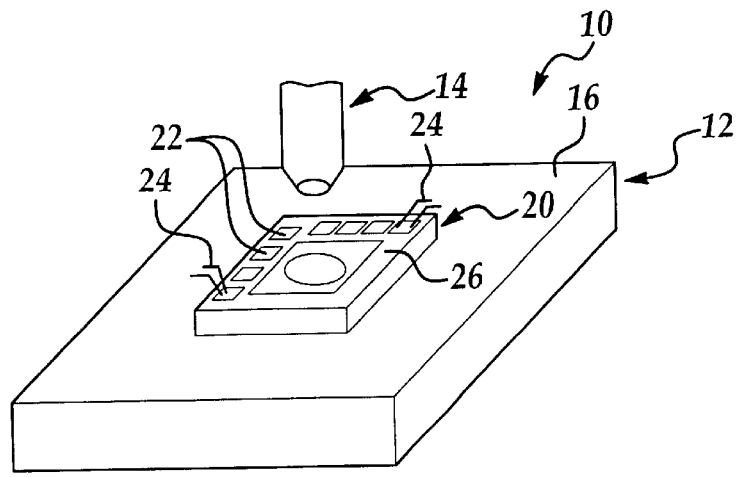
FIG. 1 is an illustration of a conventional test set-up for failure analysis of an IC chip connected to a test circuit by bonding wires.
Figure 2:
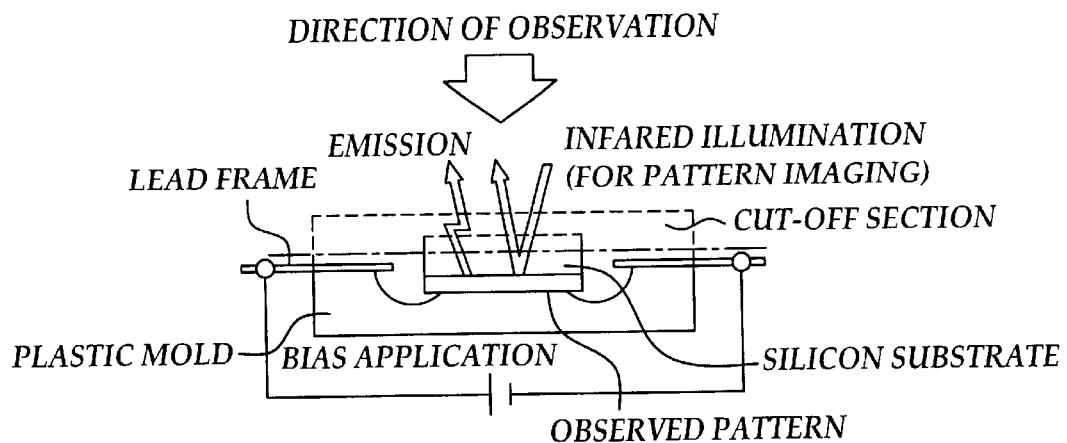
FIG. 2 is an illustration of a conventional test set-up for failure analysis by an emission microscopic method conducted on the backside of the IC device.
Figure 3:
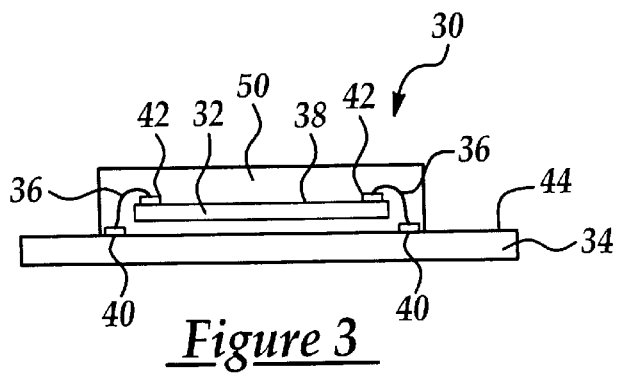
FIG. 3 is an enlarged, cross-sectional view of a present invention ball grid array package mounted on a substrate.

Referring now to FIG. 3 wherein a present invention ball grid array package 30 is shown. The BGA package 30 is formed by a conventional technique in which an IC chip 32 is first attached to a substrate 34 by a plurality of bonding wires 36. The bonding wires 36 connect each of a plurality of bond pads 42 on the top surface 38 of the IC chip 32 along the periphery of the chip to each of a plurality of conductive pads 40 on the substrate such that electrical communication between the chip and outside circuit can be established. The plurality of conductive pads 40 is further connected to a plurality of conductive runners leading to the periphery of the top surface 44 of the substrate 34. The IC chip 32 and the top surface 44 of the substrate are then encapsulated in a plastic molding compound 50 for forming the BGA package 30. The plastic molding compound 50 provides protection from the environment, and particularly from moisture and mechanical abrasion. The IC chip 32 may be first mounted to the substrate 34, prior to the wire bonding process, by a thermally conductive paste material for improved heat dissipation when the IC chip is in use.

Figure 4:
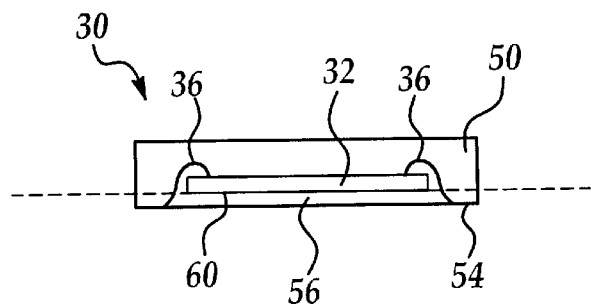
FIG. 4 is an enlarged, cross-sectional view of the ball grid array package of FIG. 3 after the substrate is mechanically removed.
Figure 5:
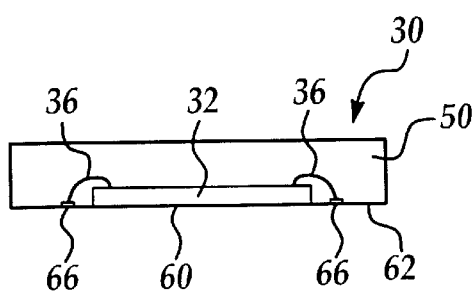
FIG. 5 is an enlarged, cross-sectional view of the ball grid array package of FIG. 4 after the molding compound on the backside of the chip is polished away.

The present invention novel method for preparing a sample for conducting a backside failure analysis can now be described according to FIGS. 4, 5 and 6. In the first step of the present invention novel method for sample preparation, the substrate 34 is mechanically removed from the encapsulating molding compound 50 by either shearing it off or tearing it off. A new surface 54 on the plastic molding compound 50 is thus produced. Ends of the bonding wires 36 are further shown in the newly created surface 54. At this stage of the sample preparation process, a layer of the plastic molding compound 56 still covers the backside 60 of the IC chip 32. The layer 56 of the plastic molding compound prevents the observation of the backside 60 of the IC chip 32 during a failure analysis and thus must be removed.

A mechanical method, such as a polishing method, and more preferably a chemical mechanical polishing method can be used to grind away or remove layer 56 from the BGA package 30. A new surface 62 of the plastic molding compound 50 is thus prepared which is in the same plane with the backside surface 60 of the IC chip 32. It should be noted that, by utilizing a chemical mechanical polishing method, not only the polishing process can be accomplished in a short period of time, a clean surface which has the ends 66 of the bonding wires 36 exposed in the plastic molding compound 50 is also achieved. The polished ends 66 of the bonding wires 36 has a diameter of about 20 $\mu$m which provides a readily accessible connection size for feeding signals into the chip 32 by probe tips which normally have a diameter of only 5 $\mu$m.

Figure 6:
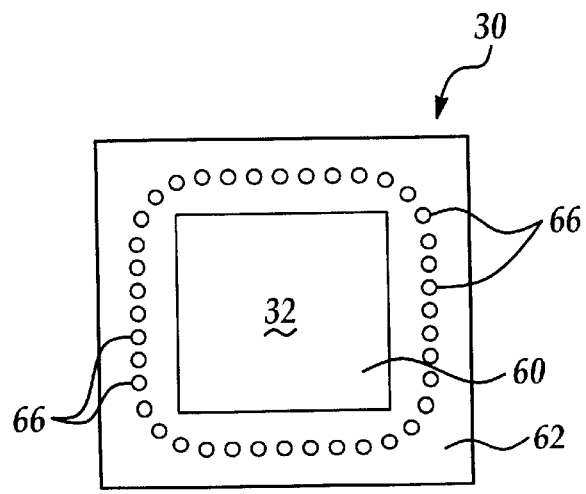
FIG. 6 is a plane view of the backside of the IC chip with wire bonds shown in the encapsulating molding compound.

As shown in FIG. 6 in a plane view of the BGA package 30, the polished ends 66 of the bonding wires 36 are exposed along a periphery of the BGA package 30 such that they can be easily probed by using probe needles for testing. Another advantageous connection method for failure analysis is wire bonding performed by a bonder to the ends 66 such that a bias voltage may be fed into IC chip 32. When the bias voltage is fed into chip 32, with the backside 60 of the chip exposed, any failure sites in the surface layer of the chip can be readily observed with naked eyes or with a microscope, as that previously described.

The present invention novel method of conducting a backside failure analysis on a ball grid array package has therefore been amply described in the above descriptions and in the appended drawings of FIGS. 3~6.

While the present invention has been described in an illustrative manner, it should be understood that the terminology used is intended to be in a nature of words of description rather than of limitation.

Furthermore, while the present invention has been described in terms of a preferred embodiment, it is to be appreciated that those skilled in the art will readily apply these teachings to other possible variations of the inventions.

What is claimed is:

1. A method for conducting backside failure analysis on a ball grid array (BGA) package comprising the steps of:
   providing a BGA package which comprises an IC chip encapsulated in a molding compound and joined to a top surface of a substrate by said molding compound, said IC chip having a backside facing said substrate and an active side,
   separating said substrate from said IC chip by severing a joint between said top surface of the substrate and said molding compound,
   removing molding compound from said backside of said IC chip such that said backside of the IC chip and a plurality of bonding wires surrounding said chip are exposed,
   contacting said plurality of bonding wires with a plurality of probes such that electrical signals are fed into said IC chip, and
   observing failure sites on said exposed backside of the IC chip.

2. A method for conducting backside failure analysis on a ball grid array package according to claim 1 further comprising the step of electrically connecting a plurality of bond pads on said IC chip to a plurality of conductive pads on said top surface of the substrate by wire bonding means.

3. A method for conducting backside failure analysis on a ball grid array package according to claim 1 further comprising the step of electrically connecting a plurality of bond pads on said IC chip to a plurality of conductive pads on said top surface of the substrate by wires that comprises gold.

4. A method for conducting backside failure analysis on a ball grid array package according to claim 1 further comprising the step of mechanically separating said substrate from said IC chip.

5. A method for conducting backside failure analysis on a ball grid array package according to claim 1 further comprising the step of tearing said substrate from said IC chip.

6. A method for conducting backside failure analysis on a ball grid array package according to claim 1 further comprising the step of removing said molding compound from said backside of the IC chip by mechanical means.

7. A method for conducting backside failure analysis on a ball grid array package according to claim 1 further comprising the step of removing said molding compound from said backside of the IC chip by a polishing method.

8. A method for conducting backside failure analysis on a ball grid array package according to claim 1 further comprising the step of removing said molding compound from said backside of the IC chip by a chemical mechanical polishing method.

9. A method for conducting backside failure analysis on a ball grid array package according to claim 1 further comprising the step of contacting said plurality of bond wires with a plurality of probe tips.

10. A method for conducting backside failure analysis on a ball grid array package according to claim 1 further comprising the step of contacting said plurality of bond wires with wire bonds from a bonder.

11. A method for conducting backside failure analysis on a ball grid array package according to claim 1 further comprising the step of feeding a bias voltage into said IC chip through said plurality of probes.

12. A method for conducting backside failure analysis on a ball grid array package according to claim 1 further comprising the step of observing said failure sites on said exposed backside of the IC chip by a microscope.

13. A method for observing failure sites on the backside of a ball grid array (BGA) package comprising the steps of:
   providing a BGA package of an IC chip encapsulated in a molding compound, said IC chip being joined to a substrate by a layer of said molding compound and by a plurality of bonding wires,
   severing a joint formed between said layer of molding compound and a top surface of said substrate,
   mechanically removing said layer of molding compound from said backside of said IC chip to expose said backside of the IC chip and said plurality of bonding wires,
   feeding a bias voltage into said IC chip through said plurality of bonding wires, and
   observing failure sites on said backside of the IC chip.

14. A method for observing failure sites on the backside of the ball grid array (BGA) package according to claim 13 further comprising the step of joining said IC chip to said substrate by a plurality of bonding wires that comprises gold.

15. A method for observing failure sites on the backside of the ball grid array (BGA) package according to claim 13 further comprising the step of encapsulating said IC chip in a molding compound that comprises plastic.

16. A method for observing failure sites on the backside of the ball grid array (BGA) package according to claim 13 further comprising the step of severing said joint between said layer of molding compound and said backside of said IC chip by tearing said IC chip from said substrate.

17. A method for observing failure sites on the backside of the ball grid array (BGA) package according to claim 13 further comprising the step of removing said layer of molding compound from said backside of the IC chip by a chemical mechanical polishing method.

18. A method for observing failure sites on the backside of the ball grid array (BGA) package according to claim 13 further comprising the step of feeding said bias voltage into said IC chip through a plurality of probe tips.

19. A method for observing failure sites on the backside of the ball grid array (BGA) package according to claim 13 further comprising the step of feeding said bias voltage into said IC chip by contacting said plurality of bonding wires with a bonder.

20. A method for observing failure sites on the backside of the ball grid array (BGA) package according to claim 13 further comprising the step of observing said failure sites on said backside of the IC chip by an optical means.

* * * * *